United States Patent [19]

Polacin et al.

[11] Patent Number: 5,530,731
[45] Date of Patent: Jun. 25, 1996

[54] SPIRAL SCAN COMPUTED TOMOGRAPHY APPARATUS AND METHOD FOR OPERATING SAME

[75] Inventors: Arkadiusz Polacin, Erlangen; Willi Kalender, Moehrendorf, both of Germany

[73] Assignee: Siemens Aktiengesellschaft, Munich, Germany

[21] Appl. No.: 393,371

[22] Filed: Feb. 23, 1995

[30] Foreign Application Priority Data

Feb. 25, 1994 [DE] Germany ............................ 44 06 268.0

[51] Int. Cl.⁶ ....................................................... A61B 6/03
[52] U.S. Cl. ........................ 378/15; 378/901; 364/413.16
[58] Field of Search ................ 378/15, 901; 364/413.16, 364/413.17

[56] References Cited

U.S. PATENT DOCUMENTS 5,166,961  11/1992  Brunnett et al. ........................ 378/19

OTHER PUBLICATIONS

"Spiral Volumetric CT with Single–Breath–Hold Technique, Continuous Transport, and Continuous Scanner Rotation," Kalender et al., Radiology, vol. 176, No. 1, Jul. 1990, pp. 181–183.

Primary Examiner—David P. Porta
Assistant Examiner—David Vernon Bruce
Attorney, Agent, or Firm—Hill, Steadman & Simpson

[57] ABSTRACT

A computed tomography method and apparatus conduct a spiral scan of a subject wherein non-uniformities of noise and topical resolution are greatly reduced. A power spectrum $S_o$ for interpolated projections is identified, from which a frequency characteristic $H(f,\theta)$, of an optimum filter for the projections interpolated from complementary data is determined, with $$H(f,\theta) = \frac{S_o + 0.5\sigma_o^2}{S_o + (1 - 2w(\theta) + 2w^2(\theta)) \cdot \sigma_o^2}$$

with $\sigma_o^2$ being the variance of the quantum noise associated with a projection and $w(\theta)$ being the spiral weighting.

6 Claims, 2 Drawing Sheets

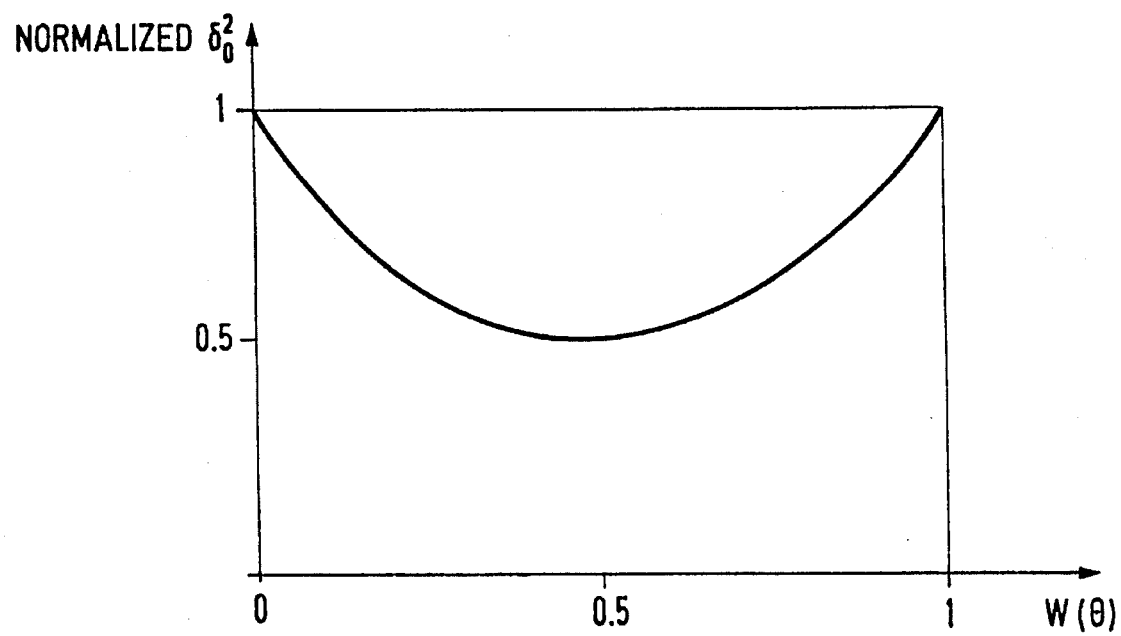
(PRIOR ART) FIG 1
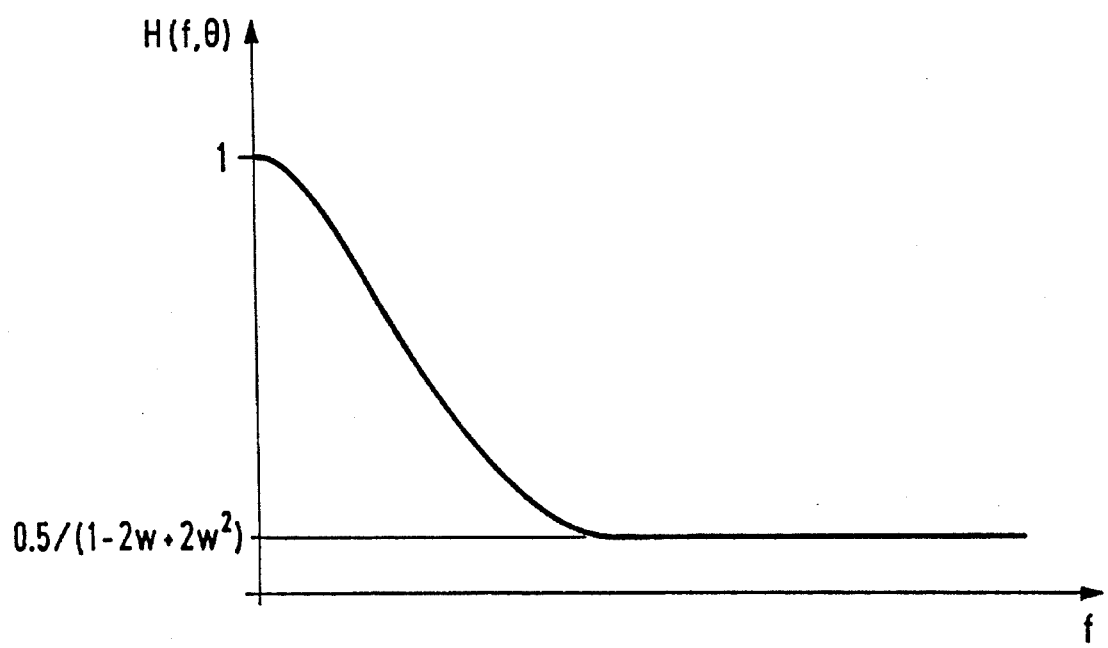
FIG 3

SPIRAL SCAN COMPUTED TOMOGRAPHY APPARATUS AND METHOD FOR OPERATING SAME

BACKGROUND OF THE INVENTION

1. Field of the Invention

The present invention is directed to a computed tomography apparatus, and in particular to a computed tomography apparatus which undertakes a spiral scan.

2. Description of the Prior Art

In x-ray computed tomography (CT), the conventional standard registration of individual slices is being replaced to an increasing degree by continuous volume exposures using spiral CT techniques. This type of scanning is also referred to as helical scanning, however, the term "spiral scanning" will be used herein. In conducting a spiral scan, a relative displacement along the z-axis is undertaken between the examination subject and the plane containing the x-ray fan beam. The x-ray fan beam is simultaneously rotated. This means that, at any given time, there will be only one point of true projection data in the planar image. Projection data for a planar slice are thus obtained by interpolating the spiral data at two points having the same rotational phase on either side of the planar slice. This procedure is repeated for all rotational phases to obtain interpolated data for 360°, sufficient to reconstruct a complete planar image. An image at the selected slice position can then be obtained by undertaking conventional image reconstruction.

Different interpolation methods are utilized for the reconstruction. Such different interpolation methods are used in an effort to influence (improve) the slice sensitivity profile and the noise properties of the image. In the attempt to fashion the profile as thin as possible, i.e., to keep the spatial resolution in z-direction optimally high, so-called 180° algorithms are recoursed. The implementation of these methods usually ensues in the form of weighting methods in order to keep the computational outlay as low as possible.

For a given series of images that are calculated with this method, however, it is frequently the case, particularly given large subjects, that the noise patterns and the image sharpness as well are non-uniformly distributed over the subject and the preferred (optimum) alignment of these distributions cyclically changes from image to image or frame to frame, a cycle being the distance that is traversed during a 360° revolution of the x-ray tube. This is illustrated in FIG. 1 on the basis of a phantom. FIG. 1 shows the curve of relative variance of the noise (i.e., normalized $\sigma_o^2$ dependent on the spiral weighting w ($\theta$)). The non-uniform distribution is considered disturbing and can impede the examination of the imaged slice; given threshold-based, three-dimensional presentations of the image data sets, it can lead to further artifacts. The degree is of different extent dependent on the specific 180° algorithm employed, but occurs in every instance.

SUMMARY OF THE INVENTION

An object of the present invention is to provide a spiral scan computed tomography apparatus and method for operating same which effectively reduce the non-uniformity in the distribution of noise and image sharpness, and which substantially eliminate these problems in most instances.

The above object is achieved in accordance with the principles of the present invention in a method and apparatus for spiral scan computed tomography wherein the power spectrum of the projections which are interpolated from complementary data is determined according to a specified equation, set forth below, wherein it is assumed that the projections and the noise are statistically orthogonal. Using this expression for the power spectrum, the frequency characteristic of an optimum Wiener filter can be identified for filtering the projections interpolated from the complementary data.

DESCRIPTION OF THE DRAWINGS

FIG. 1, as noted above, shows the relationship between noise and the spiral scan weighting factor for a phantom obtained using conventional interpolation.

FIG. 3 shows a curve for explaining the operation of the computed tomography apparatus of FIG. 2.

DESCRIPTION OF THE PREFERRED EMBODIMENTS

Figure 2:
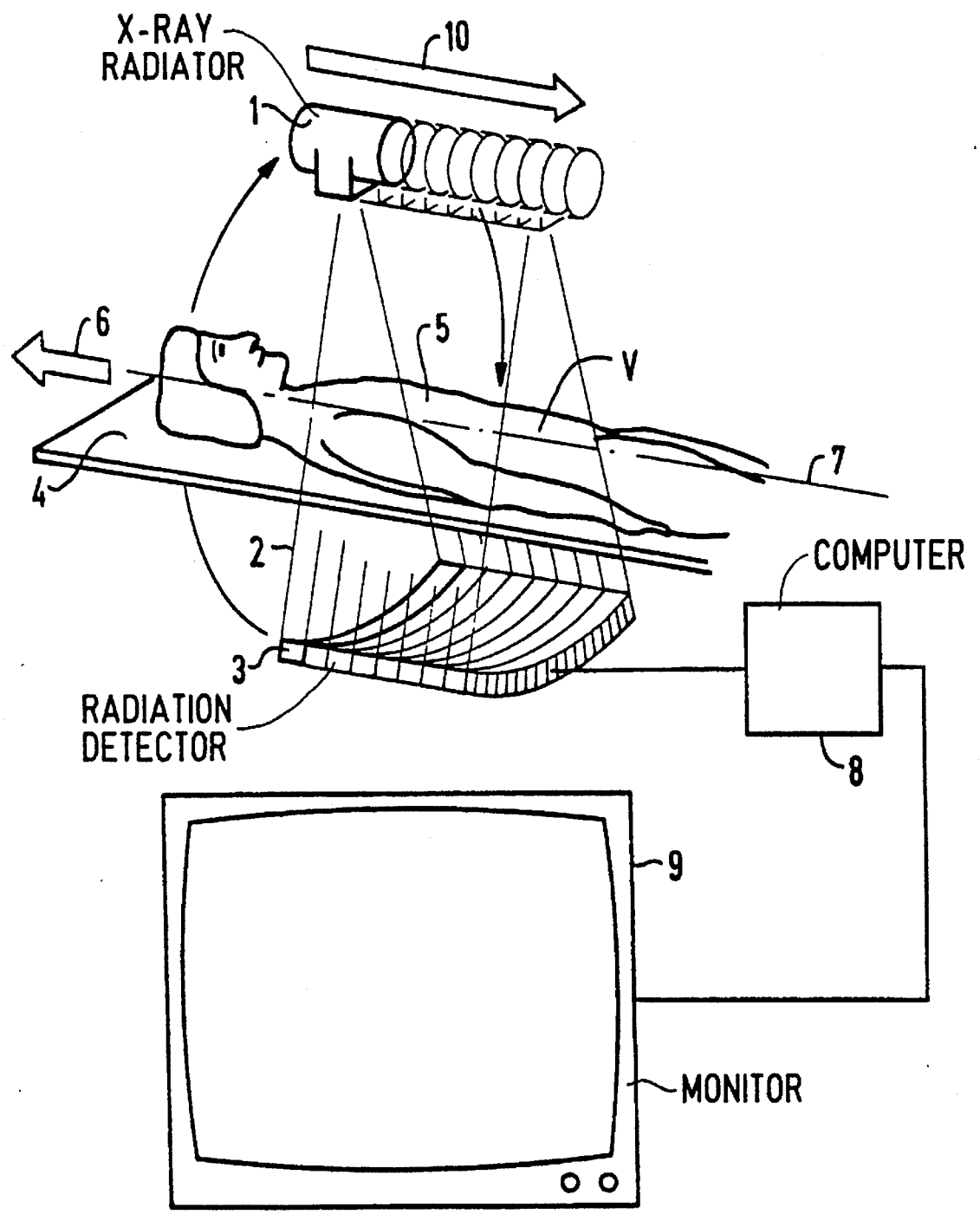
FIG. 2 is a schematic illustration of a computed tomography apparatus constructed in accordance with the principles of the present invention.

The spiral scan computed tomography apparatus shown in FIG. 2 has an x-ray radiator 1 that emits a fan-shaped x-ray beam 2 that is incident on a radiation detector 3 that is curved around the focus of the x-ray radiator 1 and is composed of a series of detector elements. A patient bed 4 having a patient 5 therein is disposed between the x-ray radiator 1 and the radiation detector 3 so that the x-rays incident on the detector 3 are attenuated by the patient 5.

For scanning a volume of the patient 5, the patient bed 4 is adjusted by a predetermined dimension in the direction of the arrow 6, while the measurement unit formed by the x-ray radiator 1 and the detector 3 rotates around the system axis 7. The data thereby generated by the detector elements of the radiation detector 3 are supplied to a computer 8 that calculates images of the patient 5 therefrom and effects their playback on a monitor 9. These images are computer tomograms of a scanned volume. Alternatively to the displacement of the patient bed 4 in the direction of the arrow 6, the measuring unit can be adjusted in the direction of the arrow 10 for scanning a predetermined volume of the patient 5, with a stationary patient bed 4.

The computer 8 comprises means for accomplishing all of the following functions.

Given the illustrated computed tomography apparatus, a planar data set is generated by complementary 180° spiral interpolation, according to the equation:

$$P_z(\gamma,\theta)=(1-w(\theta))\cdot P_{z1}(\gamma,\theta)+w(\theta)\cdot P_{z2}(\gamma,\theta) \tag{1}$$

wherein $P_z(\gamma,\theta)$=projection belonging to a planar data set for position z, having a detector subtended angle $\gamma$, and a projection angle $\theta$;

w ($\theta$)=spiral weighting: w ($\theta$)=$(z-z_1)/(0.5\ d)$ with d=table displacement (feed) per spiral revolution, and $z_1$=table position at which $P_1$ ($\gamma,\theta$) was acquired;

$P_{z1}(\gamma,\theta)$=measured data for the table position at which the projection angle $\theta$ or $\theta+\pi$ was last reached before the table position z was reached; and $P_{z2}(\gamma,\theta)$=corresponding 180° complementary data.

The resultant planar data set $P_z$ ($\gamma,\theta$) is processed with a standard convolution back-projection method to form an image. The spiral interpolation can alternatively be implemented during the back-projection by means of a weighting of the respective projection of the spiral data set. This approximative solution can be very simply implemented, namely on the existing hardware in pipeline mode, given of a pipeline processor in the computer 8. The interpolation as well as the weighting method lead to non-uniform noise distributions in the image (even for fully symmetrical subjects), whereby the weighting method produces substantially greater non-uniformities and exhibits disadvantages from the point of view of image quality. The interpolation according to equation (1) leads to noise non-uniformities because the noise level in the projections $P_z$ is dependent on the projection angle. Specifically, for $$P_{z1}(\gamma,\theta) = P_1 + n_1(\xi) \qquad (2)$$

$$P_{z2}(\gamma,\theta) = P_2 + n_2(\xi)$$

with $P_i$=deterministic part of projection i (i=1,2) and $n_i(\xi)$=random variable that models quantum noise variance $\sigma_o^2$, the variance of the interpolated projections is described as $$\text{Var } \{P_z(\gamma,\theta)\} = \sigma_o^2(1 - 2w(\theta) + 2w^2(\theta)) \qquad (3)$$

wherein Var { } designates the variance operator.

The variance as a function of the projection angle is shown in FIG. 1. One can directly see from equation (3) and FIG. 1 that the noise level significantly varies and can lead to visible inhomogeneities in the image. In order to avoid these effects, the method of the invention equalizes the noise level in all interpolated projections. This measure should not only equalize the variance but also the entire noise power spectrum in order to assure uniform noise distribution in the image. Given the assumption that projections and noise are statistically orthogonal, the power spectrum of the interpolated projections is:

$$\begin{aligned}
S\{P_z(\gamma,\theta)\} &= S\{(1 - w(\theta)) \cdot (P_1 + n_1(\xi)) + \qquad (4) \\
&\quad w(\theta) \cdot (P_2 + n_2(\xi))\} \\
&= S\{(1 - w(\theta)) \cdot P_1 + w(\theta) \cdot P_2\} + \\
&\quad (1 - w(\theta))^2 \cdot S\{n_1(\xi)\} + w^2(\theta) \cdot \\
&\quad S\{n_2(\xi)\}
\end{aligned}$$

wherein S { } is the power spectrum operator.

One can see from equation (4) that full noise power spectrum balancing is only possible when the signal and noise power spectrum do not overlap. Because this is not the case for physical reasons, a best possible balancing is made according to the least squares minimization principle. Equation (4) for w=0.5 is taken as a reference, i.e. the model signal also contains noise. This optimization leads to the following, optimum Wiener filter:

$$H(f,\theta) = \frac{S\{0.5 \cdot (P_i + P_j)\} + 0.25 \cdot [S\{n_i(\xi)\} + S\{n_j \cdot (\xi)\}]}{S\{(1 - w(\theta)) \cdot P_1 + w(\theta) \cdot P_2\} + (1 - w(\theta))^2 \cdot S\{n_1(\xi)\} + w^2(\theta) \cdot S\{n_2(\xi)\}} \qquad (5)$$

wherein H (f, $\theta$)=frequency characteristic of the optimum Wiener filter, and i,j=corresponding indices for complementary projections.

The following assumptions shall be made in order to find a practical solution:

$$S\{P_1\} = S\{P_2\} = S\{P_i\} = S\{P_j\} = S_o \qquad (6)$$

i.e., it is assumed the power spectrum of projections does not change in the z-direction in the region that is required in order to reconstruct the image for position z and, in addition, the noise is locally stationary and white with variance $\sigma_o^2$. This results in:

$$H(f,\theta) = \frac{S_o = 0.5\sigma_o^2}{S_o + (1 - 2w(\theta) + 2w^2(\theta)) \cdot \sigma_o^2} \qquad (7)$$

The frequency characteristic of a typical filter according to equation (7) is shown in FIG. 3. The projection power spectrum $S_o$ is needed for the design of an optimum filter according to equation (7). This can be found using various methods. As a result of the assumption that the noise is locally stationary, the corresponding data fragment and optimum filter length must be relatively short, presenting an extremely difficult limitation for all methods for estimating the power spectrum. Even rather rugged parametrical methods can lead to unstable situations in these circumstances. Since the power spectrum of projections only contains very low components for short data fragments, equation (7) is approximated with a stable and practical equation:

$$H^+(f,\theta) = F_o(f) \cdot \frac{0.5 - 2w(\theta) + 2w^2(\theta)}{(1 - 2w(\theta) + 2w^2(\theta))} + \frac{0.5}{(1 - 2w(\theta) + 2w^2(\theta))} \qquad (8)$$

The function $F_o$ should assure a good approximation of equation (7) and should additionally have an optimally short length of inverse Fourier transformation, i.e. number of filter coefficients. Since the function $F_o$ and the filter length are dependent on scanner parameters and on the subject, the optimization must be made separately for each instance. As one of many possible forms, for the approximation function to the Blackman window function offers very good results with relatively few filter coefficients. In this case, the filter has the following characteristic:

$$H(k,\theta) = \frac{0.5}{(1 - 2w(\theta) + 2w^2(\theta))} + \frac{0.5 - 2w(\theta) + 2w^2(\theta)}{(1 - 2w(\theta) + 2w^2(\theta))} \cdot \sum_{-N/2}^{N/2} f_k \qquad (9)$$

with $f_k$ window values.

Given a Blackman window having the length N:

$$f_k = 0.42 - 0.5 \cdot \cos\left(\frac{2\pi(k - (N-1)/2)}{N-1}\right) + 0.08 \cdot \cos\left(\frac{4\pi(k - (N-1)/2)}{N-1}\right) \qquad (10)$$

Typical filter lengths lie at 5 to 13 coefficients and supply a noise uniformity of better than 10%. Equations (8) and (9) represent a low-pass filter whose properties are modulated by $w(\theta)$. For example, the filter has no effect on the data for w=0.5, i.e for the model signal; the effect is maximum given w=0 or w=1. The effectiveness of the disclosed method is very high compared to the current standard weighting.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:

a table for supporting an examination subject extending longitudinally along an axis z;

x-ray source means for irradiating said subject with a fan-shaped x-ray beam;

radiation detector means, subtending a detector angle, for detecting x-rays in said x-ray beam attenuated by said examination subject;

means for rotating said x-ray source means and said radiation detector means around said examination subject to irradiate said examination subject from a plurality of projection angles while simultaneously effecting a relative displacement between said x-ray beam and said examination subject along said axis z for obtaining measured data from said radiation detector means in a spiral scan of said examination subject;

means for generating a planar data set $P_z(\gamma,\theta)$ for a projection having the detector angle $\gamma$ and at a projection angle $\theta$ and a position z along said axis z by complementary 180° spiral interpolation of said measured data according to $$P_z(\gamma,\theta)=(1-w(\theta))\cdot P_{z1}(\gamma,\theta)+w(\theta)\cdot P_{z2}(\gamma,\theta)$$

wherein $w(\theta)$ is a spiral weighting with $w(\theta)=(z-z_1)/0.5\,d$ with d being the relative displacement along said axis z per revolution of said x-ray source means and said radiation detector means, and $z_1$ is a position of said table at which a projection $P_{z1}(\gamma,\theta)$ was acquired, wherein $P_{z1}(\gamma,\theta)$ comprises measured data for a position of said table at which the projection angle $\theta$ or $\theta+\pi$ was last reached before the table position z was reached, and wherein $P_{z2}(\gamma,\theta)$ comprises corresponding 180° complementary data, each projection having a deterministic part and each projection having quantum noise associated therewith;

means for setting $$P_{z1}(\gamma,\theta)=P_1+n_1(\xi)$$

$$P_{z2}(\gamma,\theta)=P_2+n_2(\xi)$$

wherein $P_i$ comprises the deterministic part of projection i (i=1,2) and $n_i(\xi)$ comprises a random variable monitoring the variance $\sigma_o^2$ of the quantum noise for projection i;

means for calculating a power spectrum of each interpolated projection according to the equation $$\begin{aligned}S\{P_z(\gamma,\theta)\} &= S\{(1-w(\theta))\cdot(P_1+n_1(\xi))+\\ &\quad w(\theta)\cdot(P_2+n_2(\xi))\}\\ &= S\{(1-w(\theta))\cdot P_1+w(\theta)\cdot P_2\}+\\ &\quad (1-w(\theta))^2\cdot S\{n_1(\xi)\}+w^2(\theta)\cdot s\{n_2(\xi)\}\end{aligned}$$

wherein $S\{\ \}$ is the power spectrum operator; and means for balancing said power spectrum $S\{P_z(\gamma,\theta)\}$.

2. Computed tomography apparatus according to claim 1, wherein said means for balancing comprises a filter having a frequency characteristic $H(f,\theta)$ with $$H(f,\theta)=\frac{S_o+0.5\sigma_o^2}{S_o+(1-2w(\theta)+2w^2(\theta))\cdot\sigma_o^2}$$

wherein $$S_o=S\{P_1\}=S\{P_2\}=S\{P_i\}=S\{P_j\}.$$

3. Computed tomography apparatus according to claim 1, wherein said means for balancing comprises a filter having an approximated filter characteristic $H^+(f,\theta)$ with $$H^+(f,\theta)=F_o(f)\cdot\frac{0.5-2w(\theta)+2w^2(\theta)}{(1-2w(\theta)+2w^2(\theta))}+\frac{0.5}{(1-2w(\theta)+2w^2(\theta))}$$

wherein $F_o(f)$ comprises an approximation function.

4. A method for operating a computed tomography apparatus comprising the steps of:

supporting an examination subject on a table extending longitudinally along an axis z;

irradiating said subject with a fan-shaped x-ray beam;

detecting x-rays in said x-ray beam attenuated by said examination subject with a radiation detector which subtends a detector angle;

conducting a spiral scan of said examination subject by rotating said x-ray beam and said radiation detector around said examination subject to irradiate said examination subject from a plurality of projection angles while simultaneously effecting a relative displacement between said x-ray beam and said examination subject along said axis z for obtaining measured data from said radiation detector;

generating a planar data set $P_z(\gamma,\theta)$ for a projection having the detector angle $\gamma$ and at a projection angle $\theta$ and a position z along said axis z by complementary 180° spiral interpolation of said measured data according to $$P_z(\gamma,\theta)=(1-w(\theta))\cdot P_{z1}(\gamma,\theta)+w(\theta)\cdot P_{z2}(\gamma,\theta)$$

wherein $w(\theta)$ is a spiral weighting with $w(\theta)=(z-z_1)/0.5\,d$ with d being the relative displacement along said axis z per revolution of said x-ray source means and said radiation detector means, and $z_1$ is a position of said table at which a projection $P_1(\gamma,\theta)$ was acquired, wherein $P_{z1}(\gamma,\theta)$ comprises measured data for a position of said table at which the projection angle $\theta$ or $\theta+\pi$ was last reached before the table position z was reached, and wherein $P_{z2}(\gamma,\theta)$ comprises corresponding 180° complementary data, each projection having a deterministic part and each projection having quantum noise associated therewith;

setting $$P_{z1}(\gamma,\theta)=P_1+n_1(\xi)$$

$$P_{z2}(\gamma,\theta)=P_2+n_2(\xi)$$

wherein $P_i$ comprises the deterministic part of projection i (i=1,2) and $n_i(\xi)$ comprises a random variable monitoring the variance $\sigma_o^2$ of the quantum noise for projection i;

calculating a power spectrum of each interpolated projection according to the equation $$\begin{aligned}S\{P_z(\gamma,\theta)\} &= S\{(1-w(\theta))\cdot(P_1+n_1(\xi))+\\ &\quad w(\theta)\cdot(P_2+n_2(\xi))\}\\ &= S\{(1-w(\theta))\cdot P_1+w(\theta)\cdot P_2\}+\\ &\quad (1-w(\theta))^2\cdot S\{n_1(\xi)\}+w^2(\theta)\cdot s\{n_2(\xi)\}\end{aligned}$$

wherein $S\{\ \}$ is the power spectrum operator; and balancing said power spectrum $S\{P_z(\gamma,\theta)\}$.

5. A method according to claim 4, wherein the step of balancing said power spectrum comprises filtering the data comprising each projection with a filter having a frequency characteristic $H(f,\theta)$ with $$H(f,\theta) = \frac{S_o + 0.5\sigma_o^2}{S_o + (1 - 2w(\theta) + 2w^2(\theta)) \cdot \sigma_o^2}$$

wherein $$S_o = S\{P_1\} = S\{P_2\} = S\{P_i\} = S\{P_j\}.$$

6. A method according to claim 4, wherein the steps of equalizing comprises filtering the data comprising each projection with a filter having an approximated filter characteristic $H^+$ (f, $\theta$) with $$H^+(f,\theta) = F_o(f) \cdot \frac{0.5 - 2w(\theta) + 2w^2(\theta)}{(1 - 2w(\theta) + 2w^2(\theta))} + \frac{0.5}{(1 - 2w(\theta) + 2w^2(\theta))}$$

wherein $F_o(f)$ comprises an approximation function.

* * * * *